Figure 1:
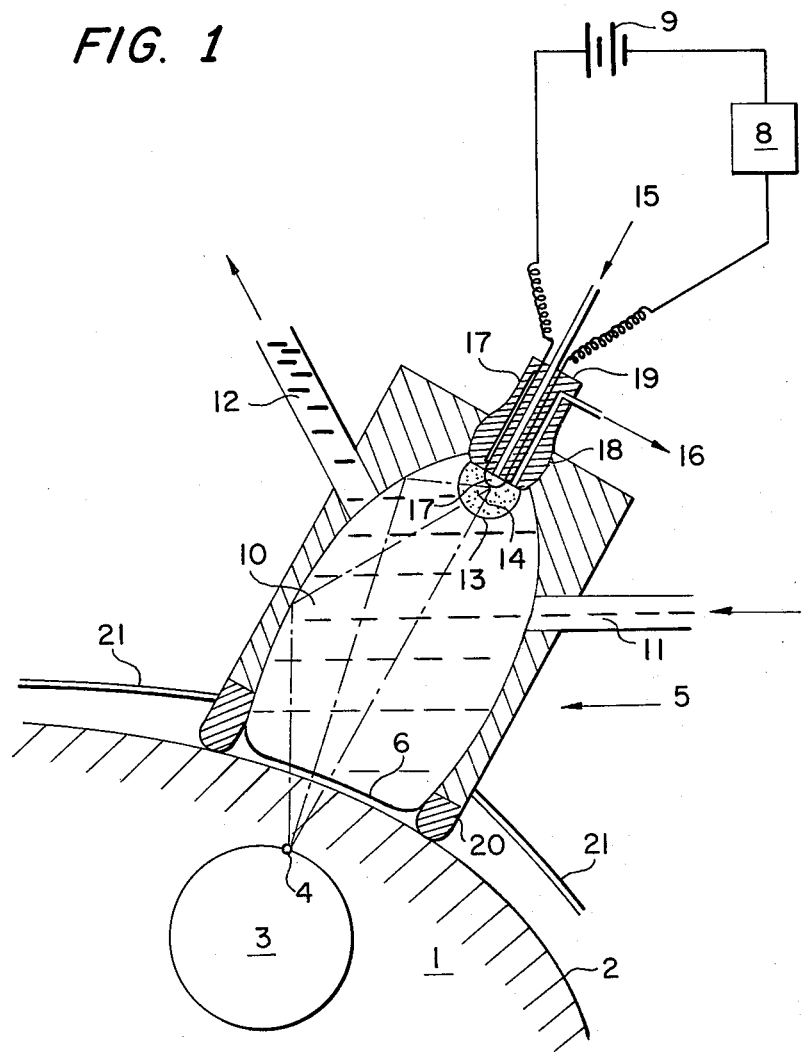

United States Patent [19]  [11] 3,970,076
Hepp et al. [45] July 20, 1976

[54] APPARATUS FOR HEART STIMULATION
[75] Inventors: Wolfgang Hepp, Immenstaad; Alexander Wirtzfeld, Thanning, both of Germany
[73] Assignee: Dornier System GmbH, Germany
[22] Filed: Feb. 4, 1975
[21] Appl. No.: 546,907

[30] Foreign Application Priority Data
Apr. 18, 1974 Germany............................ 2418631

[52] U.S. Cl................................. 128/24.5; 128/64
[51] Int. Cl.²......................................... A61H 29/00
[58] Field of Search............. 128/24.5, 24 A, 419 D, 128/419 PG, 40, 64

[56] References Cited
UNITED STATES PATENTS
3,356,086  12/1967  Behney............................ 128/24 A
3,670,736   6/1972  Panico............................ 128/419 D
3,762,420  10/1973  Moore et al..................... 128/419 D Primary Examiner—Lawrence W. Trapp
Attorney, Agent, or Firm—James E. Bryan

[57] ABSTRACT
A heart stimulator adapted to be used outside the body comprising pressure wave generating means and coupling means adapted to be placed on the surface of the body in the area of the heart without an air gap.

12 Claims, 2 Drawing Figures

APPARATUS FOR HEART STIMULATION

The present invention relates to a heart stimulator adapted to be employed from without, wherein the heart is induced to systoles in a non-bloody fashion through the chest.

The stimulation of the healthy heart starts from the sinus node in the antechamber in the form of electric signals. The latter propagate at a velocity of several m/s over the heart chamber walls and cause the contraction of the heart muscle tissue.

Each excitation formation (and excitation conduction) in the heart is based on the fact that the rest potential of one cell is reduced to a so-called threshold potential. The further depolarization of the cell which ultimately will produce the contraction, as well as the spreading of the exciting wave on to other cells, progresses independently from then on. The maintenance of the normal cell membrane depolarization is an active operation which constantly consumes energy. This process may be disturbed by different outside influences (for example by injury to the cell membrane) so that likewise a potential loss of the cell membrane is produced.

In the case of a disturbance of the natural heart stimulation it is known to maintain the heart activity by means of artificial pacemakers even over very long periods of time. It is not necessary in this connection to provide the pacemaker electrodes in proximity to the natural stimulation center in the ante-chamber. Rather it suffices to introduce the voltage impulses, at any desired point of the chamber, into the myocardium of the heart. The energy of a voltage impulse is within the range of $10^{-5}$ Ws. It is further known from cardiological practice that even a slight touch of the heart chamber walls by non-conductive heart catheters, or the pressure head alone of a contrast fluid injected into the heart chamber will suffice to induce a contraction of the heart.

An electrical stimulation introduced from outside the body and not being directed to any specific part of the heart requires high energy and is not as effective and harmless by far as direct heart stimulation by means of electrodes introduced intravenously or sutured upon the heart (myocardial electrodes).

In acute cases, the time required for the initiation of an intravenous myocardial electrical stimulation often is not available. An added factor is that these processes are relatively expensive and can be performed only by trained physicians.

In rare cases success has been achieved in stimulating a new heart activity which had either come to a standstill or become attenuated, by striking the chest of the patient. In this regard, only coincidental successes are recorded, however; a definite connection between cause and effect could not be ascertained.

Attempts to obtain an electrical stimulation of the heart by means of electrodes placed upon the chest above the heart have met with only very unsatisfactory results, for which reason such measures are hardly ever employed today.

It is the object of the present invention to provide an apparatus for heart stimulation from without in a non-bloody fashion through the chest, which apparatus is usable particularly in emergency medicinal procedures. To be electrically and mechanically stimulated is a heart chamber which is either standing still, or is beating too slowly (so-called asystoly). Causes thereof are a lack of excitation formation, or lack of ante-court/-chamber conduction.

This object is obtained, in accordance with the present invention, by means of a pressure wave generator and a coupling device which is adapted to be placed upon the surface of the body in the area of the heart and without an air gap.

Pressure waves emanating from the pressure wave generator exert mechanical stimuli onto the chamber wall of the heart which lead to heart stimulation. By means of the pressure wave generator, impulses may be periodically produced without danger to the patient and personnel until either the heart activity is maintained spontaneously, or stimulation can be undertaken with an artificial pacemaker.

In an advantageous embodiment of the present invention, the pressure waves are produced by means of a spark discharge. Pressure waves also may be produced by means of a projectile which strikes upon a reflecting plate; by means of a drop of water discharging from a water cannon at high velocity and striking upon a liquid, and by means of wire explosion and an explosive charge. If, however, a portable apparatus is required for the heart stimulation for use in an emergency, the generation by means of a spark discharge is preferred because of the improved transportability of the apparatus.

Also in an advantageous embodiment of the present invention, the side of the coupling device facing the body of the patient has an elastic membrane which is provided with a metallic layer by vaporization. The metallic layer and the coupling device that also preferably is of metal prevent the emergence of electromagnetic waves and thus act like a Faraday cage.

Furthermore it is advantageous, according to the present invention, that the edge of the coupling device facing the body is elastic and that the coupling device is adapted to be attached to the body by means of a band. Such elastic bands, which are approximately as wide as a hand, are employed, for example, for recording electrocardiograms.

In a further advantageous embodiment of the present invention, the coupling device focuses the pressure waves at the sine node of the heart. For this purpose, the coupling device may be so designed, for example, as to be circular in cross-section and elliptical in longitudinal cross-section, whereby the pressure wave generator is located in one focal point of the ellipse, and the sine node of the heart is located in the other focal point of the ellipse. The energy density of the pressure waves may be kept small by the focusing on the chamber wall within the area of biological boundary surfaces (lungs, bronchi, veins, ribs). Examinations concerning the effect of high energy shock waves on biological tissues have shown that a shock wave charge does not necessarily produce damage to the organism. It results therefrom that the pressure waves being weak as compared to the shock waves do not have any undesirable side effects. The energy density at the locus of the stimulatable tissue need not be very high, thereby precluding any danger to the aforementioned boundary surfaces. Reflections at the ribs lead to a decrease of the usable pressure wave energy but otherwise have no adverse effect.

Moreover, it is advantageous that the coupling device is filled with water or the like and comprises at least one water inlet and water outlet. The use of water as a coupling medium is advantageous since the passage of the pressure waves from the water bath into the body tissue takes place nearly reflection-free because of the equality of the acoustic impedances. Due to the inflow and outflow of the water, the water bath is kept at a constant temperature. During water circulation, the spark path operates continuously at constant electrical conditions. Grounding electrodes in immediate or direct proximity to the spark path eliminate any danger to patients and personnel. Even a slight excess pressure of the water in the coupling device will suffice to place the membrane against the surface of the body without an air gap.

In yet another advantageous embodiment of the present invention, the spark path in the coupling device is provided for by means of a ball-and-socket joint and a sliding bearing. By means thereof it is possible to locally change the starting point of the pressure waves within certain limits so that a single coupling device is usable for patients with different anatomical conditions.

Additionally it is advantageous, according to the present invention, that the spark path is surrounded by an elastic membrane filled with an inert gas. Thereby shock waves will be reflected at the phase border and will not penetrate into the water bath. In order that the spark discharge can take place at constant electrical conditions, feed lines and discharge lines for the exchange of the inert gas are provided.

Figure 2:
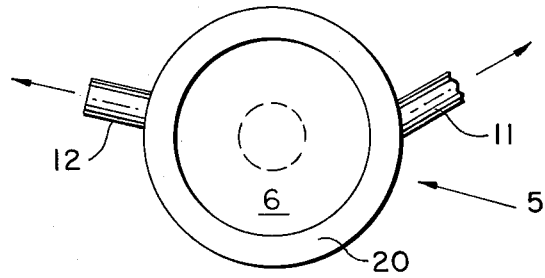

Further advantages, features and possibilities of use of the present invention will become more apparent from the following description of the accompanying drawings, in which FIG. 1 is a view in cross-section of an apparatus according to the present invention, and FIG. 2 is a bottom view of the apparatus of FIG. 1.

FIG. 1 illustrates an inventive apparatus for the heart stimulation in a cross-sectional view thereof. Shown in the figure is a human body identified with reference numeral 1, the body surface being represented by reference numeral 2, and the heart being identified with reference numeral 3. At the heart is the heart muscle 4. On the body surface 2 within the area of the heart 3 is a coupling device 5 which is closed off with respect to the body 1 by means of an elastic membrane 6. The coupling device 5 has a circular configuration in cross-section as shown in FIG. 2, and in the longitudinal cross-section shown it has an elliptical shape. In its spatial form, the coupling device 5 is thus part of a rotational ellipsoid. In the coupling device 5 is a pressure wave generator 7 which is constructed as a spark path and which is supplied by a current source 9 via a control unit 8. The coupling device 5 is filled with a liquid medium 10 (for example water). Provided for the inflow of the water 10 is an inflow line 11, and for the discharge thereof a discharge line 12. Regulating means (not shown) in the inlet and outlet of the water assure that the water in the coupling device 5 will remain at a constant temperature which corresponds approximately to the body temperature of the patient to be treated, and will be constantly available under pressure so that the membrane 6 is pressed without an air gap against the body surface 2.

In order to prevent pressure waves from penetrating into the water bath 10 and from there into the body, the spark path 7 is within an elastic membrane 13 which is filled with an inert gas 14. For purposes of constant circulation of the inert gas, the lines 15 and 16 are provided. The circulation of the inert gas is advantageous since it assures that the spark discharge takes place at all times under the same physical conditions. A head 17 connected with the spark path 7 forms — together with a recess in the coupling device 5 — a ball-and-socket joint 18, which renders possible an angular movement of the spark path 7. Further provided in the head 17 is a sliding bearing 19 so that the spark path 7 can be brought to other points in the coupling device 5. By varying the position of the spark path 7 in the coupling device 5, it is possible that the pressure waves impinge upon the heart muscle in a focused manner. The effectiveness is greatest when the spark path 7 is positioned in one focal point of the coupling device 5 forming an ellipse, and when the heart muscle is in the other focal point of the ellipse. An optimal focusing is thereby obtained.

The edge 20 of the coupling device 5 is an elastic ring. Further attached to the coupling device 5 is a band 21 which is approximately as wide as a hand and which surrounds the body of the patient to be treated.

During use of the device, the spark path 7 is periodically supplied (at the frequency of the natural pulse) with electric energy from the current source 9. The electric energy is transformed to the required voltage (about 1 kV), rectified, and stored in a capacitor. These capacitors are discharged within the required periodic time of approximately 1 second via the spark path. The duration of the impulse is about 0.5 to 2 ms.

It will be obvious to those skilled in the art that many modifications may be made within the scope of the present invention without departing from the spirit thereof, and the invention includes all such modifications.

What is Claimed is:

1. A heart stimulator adapted to be used outside the body comprising pressure wave generating means and coupling means adapted to be placed on the surface of the body in the area of the heart without an air gap.

2. A heart stimulator according to claim 1 in which said pressure wave generating means is a spark discharge.

3. A heart stimulator according to claim 2 including grounding electrodes in proximity to the spark path.

4. A heart stimulator according to claim 2 including a ball-and-socket joint means and a sliding bearing means whereby said spark path is displaceable.

5. A heart stimulator according to claim 2 including elastic membrane means filled with an inert gas surrounding the spark path.

6. A heart stimulator according to claim 5 including inlet and outlet lines for circulating said inert gas.

7. A heart stimulator according to claim 1 in which said coupling means includes elastic membrane means provided with a vapor-deposited metallic layer on a part thereof adapted to be placed on the surface of the body.

8. A heart stimulator according to claim 1 in which said coupling means includes an elastic edge adapted to contact the body, and including band means for securing said coupling device to the body.

9. A heart stimulator according to claim 1 in which said coupling means focuses pressure waves on the heart muscle.

10. A heart stimulator according to claim 1 in which said coupling means is circular in transverse cross-section and elliptical in longitudinal cross-section, said pressure wave generating means being located in one focal point of the ellipse and the heart muscle in the other focal point of the ellipse.

11. A heart stimulator according to claim 1 in which said coupling means is filled with water and includes inlet and outlet means.

12. A heart stimulator according to claim 11 including means for circulating said water.

* * * * *